US006853453B2

(12) United States Patent
Kwon

(10) Patent No.: US 6,853,453 B2
(45) Date of Patent: Feb. 8, 2005

(54) VIDEO CAMERA-BASED VISIBILITY MEASUREMENT SYSTEM

(75) Inventor: Taek Mu Kwon, Duluth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 10/330,831

(22) Filed: Dec. 26, 2002

(65) Prior Publication Data

US 2003/0174332 A1 Sep. 18, 2003

Related U.S. Application Data

(63) Continuation of application No. 09/267,035, filed on Mar. 12, 1999, now abandoned.

(51) Int. Cl.[7] ............................................. G01N 21/59
(52) U.S. Cl. ........................................................ 356/437
(58) Field of Search ........................................ 356/437

(56) References Cited

U.S. PATENT DOCUMENTS

| | | | |
|---|---|---|---|
| 2,198,971 A | 4/1940 | Neufeld | 356/437 |
| 3,694,936 A | * 10/1972 | Ling et al. | 356/437 |
| 4,200,398 A | 4/1980 | Persson et al. | 356/437 |
| 4,216,498 A | 8/1980 | Evans et al. | |
| 4,921,349 A | 5/1990 | Richards | 356/348 |
| 5,987,152 A | 11/1999 | Weisser | 382/104 |
| 6,128,088 A | 10/2000 | Nishiwaki | |

FOREIGN PATENT DOCUMENTS

DE 3801368 7/1989

OTHER PUBLICATIONS

"Glossary of Meteorology," *American Meteorological Society*, 7 pgs., (1959).
Duntley, S., "The Reduction of Apparent Contrast by the Atmosphere," *Journal of the Optical Society of America*, vol. 38, No. 1–12, pp. 179–191, (1948).
Gonzalez, R. et al., *Digital Image Processing*, Addison–Wesley Publishing Company, pp. 1–52 (1992).
Ortega J. M.; Rheinholdt, W.G., *Iterative Solution of Non–Linear Equations and Several Variables*, Academic Press: San Diego, Ca, 1970, pp. 240–280.
W.E. Knowles Middleton, *Vision Through Atmosphere*, University of Toronto Press: Canada, Table of Contents; pp. 3–17; 60–136; 175–214 (1968).

* cited by examiner

*Primary Examiner*—Richard A. Rosenberger
(74) *Attorney, Agent, or Firm*—Merchant & Gould P.A.

(57) ABSTRACT

A video camera based atmospheric visibility measurement system that is capable of providing automated measurements of atmospheric visibility during both the day and night. For daylight measurements, the system views an image that has contrasting portions. A representative contrast signal is generated for contrasting portions of the images. The representative contrast number is used to generate an exponential curve of contrast levels versus distance. Atmospheric visibility is determined by detecting where the exponential curve reaches a threshold of visibility.

12 Claims, 10 Drawing Sheets

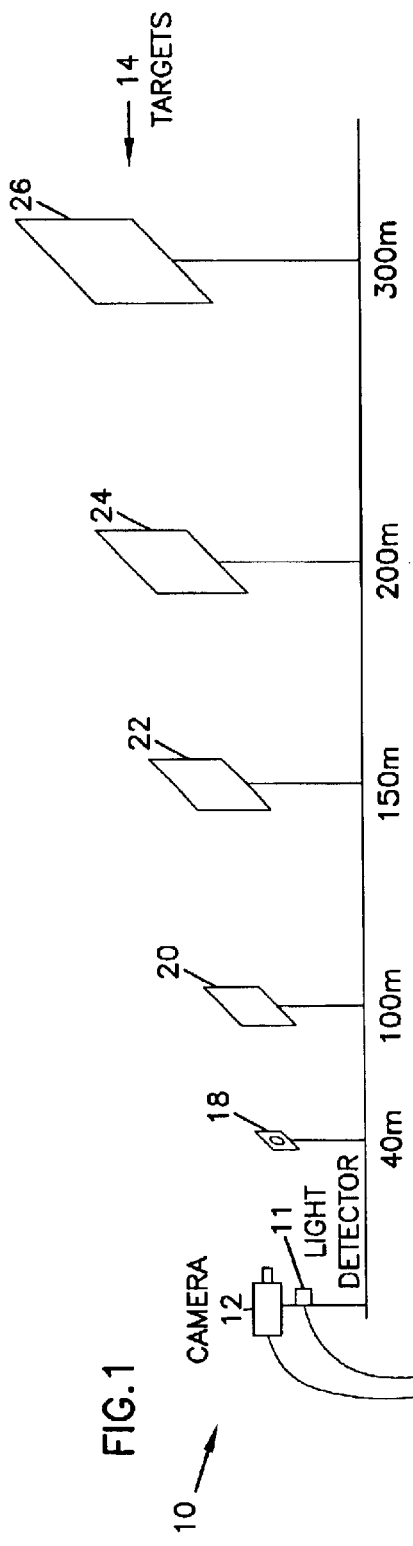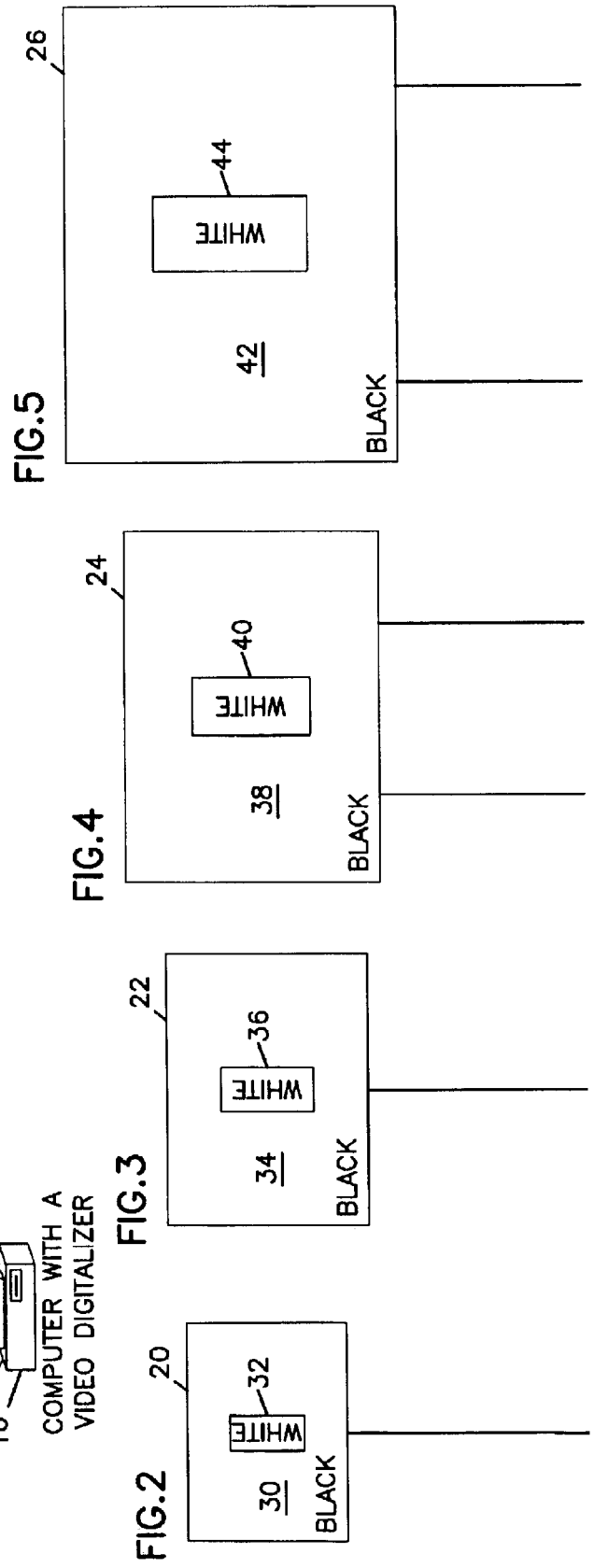

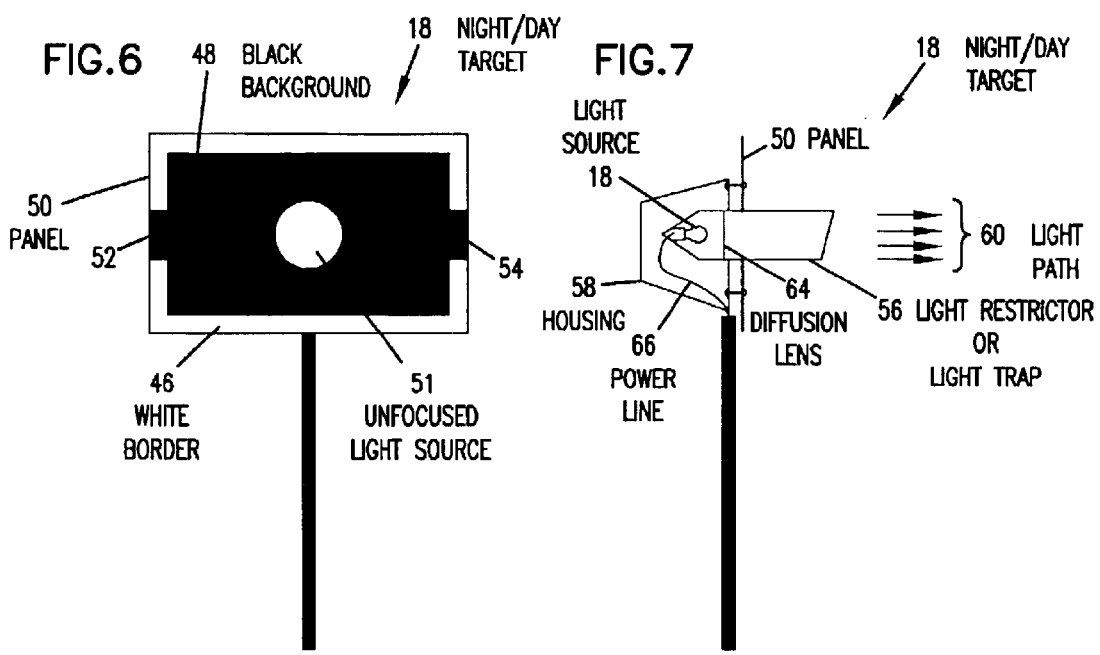
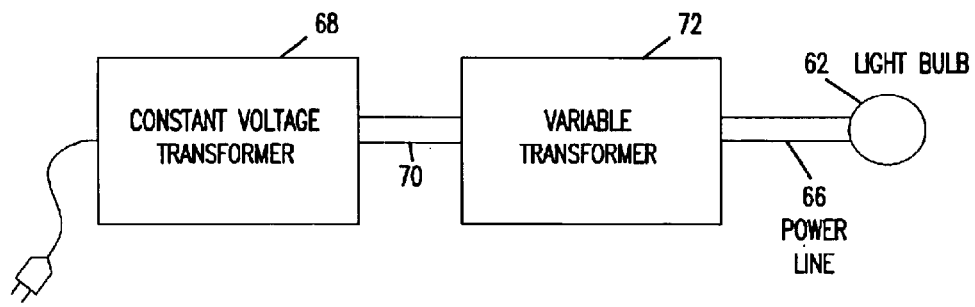

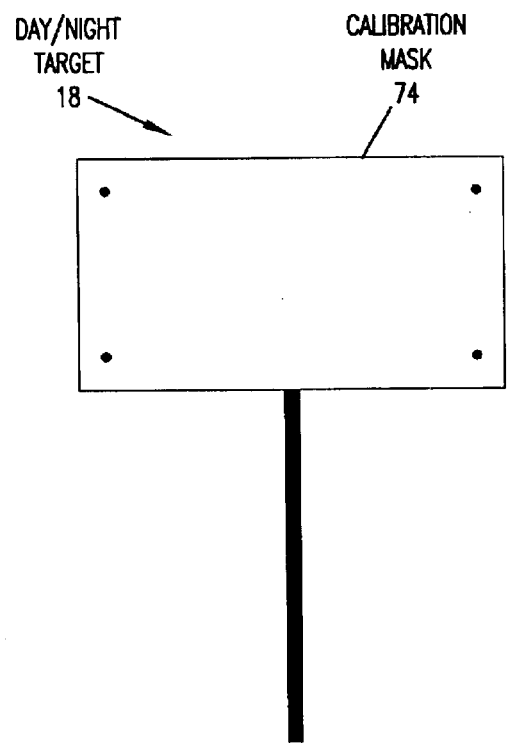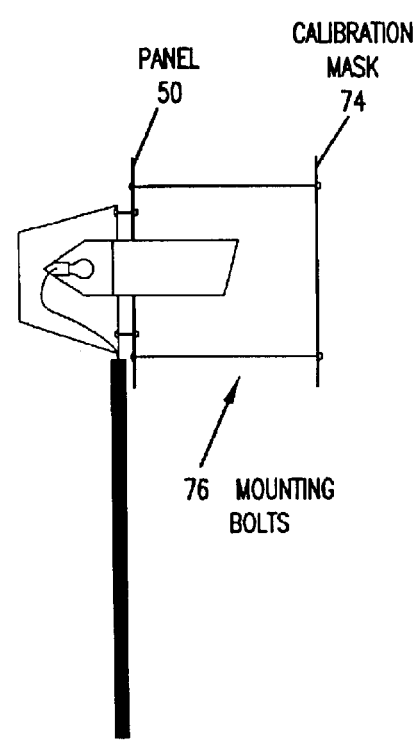

VIDEO CAMERA-BASED VISIBILITY MEASUREMENT SYSTEM

This application is a continuation of application Ser. No. 09/267,035, filed Mar. 12, 1999, now abandoned, which application(s) are incorporated herein by reference.

BACKGROUND OF THE INVENTION

A. Field of the Invention

The present invention pertains generally to automated methods of measuring atmospheric visibility and, more particularly, to a video camera-based system for measuring atmospheric visibility.

B. Description of the Background

Visibility conditions are affected by the structure and elements of the atmosphere, such as fog, snow, wind, dust, and other adverse conditions. Visibility has been defined as the greatest distance at which an object of specified characteristics can be see and detected by the naked eye. See *American Meteorological Society*, Glossary of Meteorology, 1989, and W. E. Knowles Middleton, *Vision Through Atmosphere,* 1968, University of Toronto Press. Atmospheric visibility is normally expressed in distance, such as meters or yards, or at greater distances in kilometers or miles. Atmospheric visibility at night is determined by measuring the distance from a point of light of a given intensity to a point where the light source is just detectable by the human eye. See *American Meteorological Society* and W. E. Knowles Middleton, supra. Currently, most visibility measurement instruments are based on the principle of measuring forward or backward light scattering effects.

As light is scattered by atmospheric particles, scattered light meters record the visibility. There are a number of problems, however, with measuring visibility using scattered light meters (SLMs). First, light scattering by atmospheric particles such as atmospheric moisture is only one of the effects that reduces visibility in the atmosphere. For example, absorption or obscuration by large particulate matter such as snow, dust, etc. can have a much greater effect on atmospheric visibility than simple light scattering of smaller particles, such as atmospheric moisture that causes fog. Hence, light scattering of smaller particles only contributes partially to atmospheric visibility effects.

Additionally, SLMs typically only measure the light scattering effects of a small region of a few cubic inches located adjacent the SLM. If the local region adjacent the SLM deviates from the overall visibility, such as the visibility along a road at a distance of up to 300 meters, the SLM will report a very large error. Local regions of fog, blowing snow, local dust storms and other effects can cause the visibility to vary drastically from one spot to another. Hence, SLMs are prone to providing incorrect readings of visibility in adverse conditions.

While SLMs provide a fairly accurate measure of light scattering, and hence visibility under conditions of fog where atmospheric moisture is the primary contributing factor for low visibility, SLMs may provide a high margin of error for visibility measurements under rain and snow conditions for the reasons as set forth above. One of the reasons is that there is a less significant correlation between atmospheric visibility and the light scattering effect under rain and snow conditions. Additionally, the light scattering effect varies with different types of atmospheric particles. In order for SLMs to correctly measure visibility, the SLMs need to recognize both the types and size of particles and self-calibrate to adjust the measurement of atmospheric visibility according to the different scattering properties of atmospheric particles to provide a proper measurement. The ability to determine the types and sizes of particles present in the atmosphere, as well as the ability to self-calibrate an SLM according to the types and sizes of particles detected, would greatly increase the cost of the SLM and would most likely provide results that are still prone to errors.

Hence, atmospheric visibility that is perceived by the human eye can often be very different from the visual range measured by SLMs due to the basic operating principles of the SLM. As pointed out above, SLMs only measure one physical property of the atmosphere, and only measure that property in a small region that is located near the SLM. Additionally, SLMs do not provide an easy way to verify the correctness of the visibility that is reported by the SLM. Since visibility is often used to make critical decisions in transportation applications, such as road closures or speed limit decisions, it is vitally important that such decisions be verified.

Statistical reliability has been used as an alternative to verification in some instances. For example, several SLMs may be installed in the area in which atmospheric visibility is to be measured to increase the statistical reliability of the measurements that are made. Since SLMs are very expensive, this greatly increases the cost, and the SLMs still suffer from the inherent problems indicated above. Moreover, SLMs require a high degree of precision in the alignment of the transmitter and receiver optics which additionally adds to the cost of the SLM systems.

It is against this background, and the limitations and problems associated therewith, that the present invention has been developed.

SUMMARY OF THE INVENTION

The present invention overcomes the disadvantages and limitations of the prior art by providing a system that can accurately measure atmospheric visibility in a manner that is similar to the manner in which the human eye perceives atmospheric visibility. The present invention can also utilize existing equipment that is used for other purposes, such as a video camera, which will additionally allow verification of automatic visibility measurements made by the system.

The present invention may therefore comprise a system for measuring atmospheric visibility comprising, at least two targets having contrasting portions, a video detector that is aligned to detect the contrasting portions of the targets and that generates a signal indicative of contrast levels of the contrasting portions of the target, and a processor that generates a representative contrast number from the contrast levels detected for each target, and that generates a nonlinear curve based on the representative contrast number detected for each target and the distance of each target from the video detector, and that generates a visibility number based on the slope of the exponential equation.

The present invention may also comprise a system for measuring atmospheric visibility in a predetermined region from a predetermined location comprising, a plurality of targets having visible contrasting portions, the plurality of targets disposed such that each target of the plurality of targets is disposed in the predetermined region at a distance from the predetermined location, an image detector disposed at the predetermined location that is aligned to view the plurality of targets and that generates an image signal that is indicative of contrast levels of the contrasting portions, and a processor that generates a visibility range measurement by determining a distance at which the contrast levels can just be distinguished based on the slope of an exponential curve that is representative of an average of the highest detected contrast levels for each of the targets versus the distance of the targets from the detector.

The present invention may further comprise a system for measuring atmospheric visibility in low light level conditions comprising, a light source that provides an unfocused column of light having a substantially spatially uniform intensity, an image detector that generates an image signal that has spatial intensity values of the light source that vary in accordance with an exponential curve having an exponential constant that is proportional to visibility, and a processor that generates a visibility measurement by determining the exponential constant from the spatial intensity values of the light source.

The present invention may further comprise an atmospheric visibility system, a plurality of targets comprising a first target having contrasting portions of a first predetermined size that are visible by an image detector for use in the visibility system at a first predetermined distance from the image detector, and at least one additional target having contrasting portions of a second predetermined size at a second predetermined distance from the image detector, such that the first predetermined size at the first predetermined distance and the second predetermined size at the second predetermined distance appear substantially the same.

The present invention may further comprise a target of an atmospheric visibility system that can be used at night to detect atmospheric visibility comprising a light source that has a substantially uniform spatial intensity, and a light restrictor disposed to provide a defined source of light from the light source that has a contrasting edge.

The present invention may further comprise a method of measuring atmospheric visibility in a region measured from a predetermined location comprising the steps of generating an image signal of a plurality of targets having contrasting portions, the plurality of targets disposed in the region at predetermined distances from the predetermined location, the image signal having intensity levels representative of the contrasting portions, generating representative contrast level signals for the plurality of targets from said intensity levels, generating an exponential curve that is indicative of said representative contrast level signal versus the distance of said plurality of targets from the predetermined location, and generating an atmospheric visibility measurement signal by locating a point on the exponential curve having a predetermined slope.

The present invention may further comprise a method of measuring atmospheric visibility in low light level conditions in a region measured from a predetermined location comprising the steps of, generating a source of light in the region at a predetermined distance from the predetermined location, the source of light having a substantially uniform spatial intensity that is sufficiently defined to produce a contrasting edge, generating an image signal that has spatial intensity values of the source of light that vary in accordance with an exponential curve having an exponential constant that is proportional to visibility, and generating a visibility measurement by determining the exponential constant and a proportionality constant for the exponential constant.

The advantages of the present invention are that it can provide very accurate measurements of atmospheric visibility during both the day and night in the same fashion that atmospheric visibility is perceived by the human eye. The system can utilize existing equipment that may be used for other purposes to reduce costs. Further, the present invention allows for manual verification which may be desired such as when important decisions need to be made regarding road closure or speed limit reductions.

BRIEF DESCRIPTION OF THE DRAWINGS

FIG. 1 is a schematic illustration of one implementation of the present invention.

FIGS. 2–5 illustrate daylight targets that can be used with the present invention.

FIG. 6 is a front view of a night target that can be used with the present invention.

FIG. 7 is a side view of a night target that can be used with the present invention.

FIG. 8 is a schematic block diagram of a power supply that can be used with the light source of the present invention.

FIG. 9 is a front view of the night target that has a calibration mask mounted on its front portion.

FIG. 10 is a side view of the night target that has a calibration mask mounted on its front portion.

DETAILED DESCRIPTION OF THE PREFERRED EMBODIMENT

Figure 11:
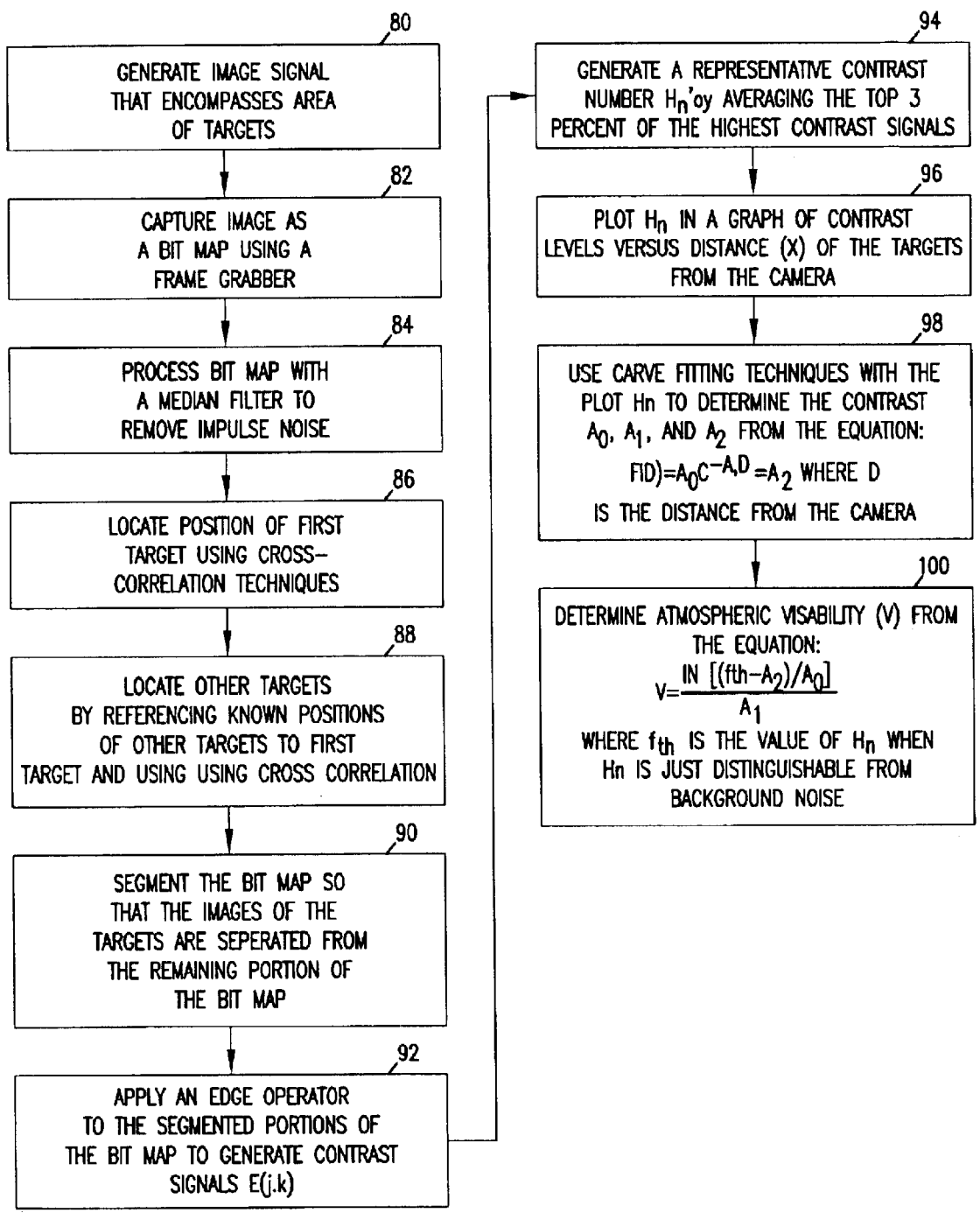
FIG. 11 is a flow diagram of the steps performed to measure atmospheric visibility during daylight.

FIG. 1 is a schematic illustration of a system 10 in which the present invention can be implemented. As shown in FIG. 1, a camera such as a video camera or digital camera is aligned to view a series of targets 14 in a region in which measurement of atmospheric visibility is desired. Camera 12 can comprise any desired detector device that is capable of detecting contrasting portions of the targets 14 during daylight hours and a light source that is provided in target 18 during low light level conditions. For example, any suitable CCD array that is focused to provide an image of the targets 14 can be utilized, including video cameras, digital cameras, scanners, or other similar devices. Camera 12 should have a built-in auto iris and back light compensation function in order to obtain a good quality picture. Camera 12 may also be housed in a defrost heater having a fan to prevent frost or fog on the lens. Compressed air may also be provided to blow the lens of the camera in order to quickly dry fogs and water and also to protect the housing lens area from snowflakes and water drops. A light level detector 11 can also be used to detect overall light conditions. Use of this detector is more fully disclosed with respect to FIG. 16.

Targets 14 are disposed at various distances or ranges from the camera 12 which is located at a predetermined location, as shown in FIG. 1 (not to scale). For example, target 18 is located at a fairly close distance to the camera 12 to ensure that at least one target is visible during extremely low visibility conditions. Target 18, for example, may be located at a distance of approximately 25–40 meters from the predetermined location of the camera 12. This is so that at least one target can be detected in very low visibility conditions. Targets 20, 22, 24, and 26 are located at greater distances along the region in which the atmospheric visibility is to be measured. For example, target 20 is located at 100 meters, target 22 at 150 meters, target 24 at 200 meters, and target 26 at 300 meters. Of course, any desired distances can be used to locate the targets and these are only examples of locations of the targets 14 from the camera 12 that provide data that is useful in measuring atmospheric visibility. In highway applications, atmospheric visibility up to 300 meters may be important. Hence, the farthest target 26 is located at approximately 300 meters from the camera 12. Also, any desired number of targets can be utilized for determining visibility during daylight hours, as long as at least two targets are provided. Of course, more accurate measurements may be obtained by using more targets as will become apparent from the description below. For nighttime visibility, only one target is required. As shown in FIG. 1, target 18 is a lighted target that provides information for nighttime visibility, as explained below.

Referring again to FIG. 1, a computer 16 that has a frame grabber (video digitizer) that is used to capture an image of the targets and to process that image to generate an atmospheric visibility measurement. The frame grabber captures a single frame from the image that is generated by the camera 12. The image is in the form of a bit map in which each picture element (pixel) has a specified intensity. The intensity of the picture element is normally digitized into an 8-bit byte so that it can have one of 0 to 255 different levels. If 24-bit color data is provided in an RGB format, it can be converted to 8-bit black and white in accordance with equation 1:

$$M = 0.299*R + 0.587*G + 0.114*B \qquad \text{Eq. (1)}$$

where M is the monochrome back and white data, R is the red component, G is the green component and B is the blue component. Equation 1 is a standard color to monochrome conversion formula.

Computer 16 of FIG. 1 can be a personal computer or any customized computing device, such as a micro-controller, or programmable logic device that is designed to perform the functions of the present invention. The frame grabber should use the same convention for capturing the image that is used by the camera 12. For example, if a video camera is used that provides an NTSC signal, the frame grabber should be able to capture images from the NTSC signal.

FIGS. 2–5 are a schematic illustration of a front view of targets 20–26 of the present invention. As seen from these figures, each of the targets increases in size as the range of the target increases from the camera 12. It is important that the camera 12 be able to view all of the targets 18–26 in a single image frame. The targets 20–26 are made so that they have an increasingly larger size as the distance at which they are deployed increases from the camera 12. As a rule of thumb, the size of the targets must be increased by a subtended angle of approximately 0.5 degrees with respect to the distance. In this manner, the resultant image of each of the targets is substantially the same size and can fit in the single frame of the camera 12.

As shown in FIG. 2, target 20 has a black background 30 with a white stripe 32 located in the center of the target running vertically. Similarly, FIG. 3 illustrates target 22 which has a black background 34 with a white stripe 36. FIG. 4 illustrates target 24 which has a black background 38 and a white stripe 40. FIG. 5 illustrates target 26 which has a black background 42 and a white stripe 44. The choice of black and white color in the targets are important, since this combination provides the highest contrast in monochrome black and white images. By providing these targets with increasing sizes so that a similar size image for each of the targets can be generated, a substantially equal amount of data can be obtained from the images of each of the targets. In this manner, a similar number of data points for contrast signals of each target can be generated for each of the targets since these targets appear to have substantially the same image size. This reduces error factors in obtaining contrast levels for each of the targets, as described below.

The targets illustrated in FIGS. 2–5 can also use a reverse contrast scheme. For example, each of the targets may utilize a white background with a black stripe. Further, a number of different stripes may be used with either contrast scheme, depending upon the number of contrast points desired, and the resolution of the camera 12. Of course, other shapes can be used, such as a black background with a white number identifying the target. The primary purpose, however, is to create contrasting edges in the image. White stripes against a black background creates the stronger contrast image and therefore provides the best edge information for measuring atmospheric visibility. Anything other than black and white can fail when the ground is covered with snow because white snow can create a strong edge or contrast at unknown distances, i.e., outside of the silhouette of the target. Additionally, if snow sticks to a target, a contrast edge can be generated between the white snow and the black background which can also serve as a contrast edge for use in accordance with the present invention.

FIG. 6 is a front view of the night/day target 18. Target 18 has a panel 50 that has a white border 46 and a black background 48. An unfocused light source 51 is located in approximately the center of the target and is surrounded by the black background 48 when viewed from the front. The unfocused light source 51 provides a substantially spatially uniform source of light in the plane of the panel 51. In other words, the intensity of the light that is emitted from the target 18 in the plane of panel 50 is substantially equal. The black background 48 of panel 50 extends to the edges of the panel at 52 and 54. Sections 52 and 54 prevent the scattering of light from the unfocused light source 51 onto the white border portion 46 along the area that traverses sections 52 and 52 and passes through the unfocused light source 51. As is disclosed below, the atmospheric visibility at night is determined by detecting the amount of light scattering of the atmosphere along a horizontal line that passes through sections 52 and 54 and the unfocused light source 51. By blackening out the areas 52 and 54, reflections from particles back to the panel 50 does not cause unwanted light scattering in the regions 52, 54.

FIG. 7 is a side view of the night/day target illustrated in FIG. 6. As shown, the panel 50 is mounted so that panel 50 surrounds the light restrictor or light trap 56. The light restrictor (light trap) 56 is painted with a non-gloss black and is attached to the housing 58 to provide a light path 60 for light emanating from the night/day target 18. Housing 58 is a waterproof housing that houses the light source 62 and a defusion lens 64. The light source 62 may comprise a simple light bulb that provides an output that is substantially uniform along the plane of the panel 50. Any non-uniformities in the light source 62 are substantially corrected by the defusion lens 64 so that the light path 60 provides a substantially uniform intensity along the plane of the panel 50. A power line 66 is attached to the light source 62 to provide power to light source 62. As disclosed below, the power provided on power line 66 remains substantially constant so that the output of the light source 62 also remains substantially constant.

The light restrictor 56 illustrated in FIG. 7 defines the light path 60 so that a contrast edge is created between the light restrictor 56 and the panel 50 when viewed from the front, as illustrated in FIG. 6. The light restrictor 56 also protects the light source 62 and the defusion lens 64 from snow and rain.

FIG. 8 is a schematic block diagram of a constant voltage power supply that is used to power a light bulb 62, that may comprise the light source of the day/night target 18 illustrated in FIG. 7. Referring again to FIG. 8, a constant voltage transformer 68 is plugged into a power source from a utility company. The utility company may provide a power source having 60 hertz AC with a voltage ranging from 95 to 130 volts. The constant voltage transformer 68 produces an output 70 that maintains a substantially constant voltage. This substantially constant voltage is applied to a variable transformer 72 which allows the user to change the voltage on power line 66 that is applied to light bulb 62. It is usually desirable to provide an output that ranges from approximately 0.7 to 2 foot candles in a light path 60 that has a diameter of approximately 8 inches. This allows the light source to provide the desired amount of light for detection by the camera 12. To provide proper measurements of visibility at night or under low light level conditions, it is important to produce a constant output from the light source along the light path 60 once the system has been calibrated. Hence, the constant voltage transformer 68 is important in providing a constant voltage to the light bulb 62 so that the light bulb 62 can provide a substantially constant output. Variable transformer 72 is useful when setting the output intensity (number of foot candles) of the light bulb 62. Also, the intensity of the light bulb 62 may decrease over time and it may be desirable to readjust the variable transformer 72 to provide the desired number of foot candle output of the light bulb 62. It may also be desirable to run the light bulb 62 at a lower voltage level. For example, the light bulb 62 may be run at 70 percent of the 117 volt RMS value of the AC signal which is approximately 74 volts RMS AC. This lengthens the life of the light bulb 62 and may provide a more uniform output of the light bulb along the spatial plane of the target panel 50.

FIG. 9 is a front view of the day/night target 18 with a calibration mask 74 mounted on the front of the target 18. As shown in FIG. 10, the calibration mask is mounted to the panel 50 of the target with mounting bolts 76. The calibration mask 74, as explained in more detail below may comprise a clear plastic material with light scattering material such as bubbles trapped inside and it is used to calibrate the system for measuring night visibility.

The operation of the system of the present invention, under both day and night conditions, is described with reference to the flow diagrams of FIGS. 11 and 12. During the day, or under conditions other than very low light level conditions, the present invention operates in the matter illustrated in FIG. 11. As indicated at step 80 of FIG. 11, the camera 12 is mounted such that it generates an image that encompasses the area in which the targets 14 are disposed. At step 82, the image is captured using a frame grabber which generates a bit map of the image. At step 84, the computer then processes the bit map image to remove impulse noise using a media filter such as disclosed by R. C. Gonzales and R. E. Woods, *Digital Image Processing*, Addison-Wesley Publishing Company, Reading, Mass., 1993. Impulse noise tends to create false edges and could lead to a distortion of the computational results of the present invention. The media filter processed image (or bit map) is referred to as the F-image, or the original image, for purposes of this description.

At step 86 of FIG. 11, the position of the first target is located using cross correlation techniques, such as those disclosed in *Digital Image Processing*, supra. Of course, any desired algorithm can be used to locate the first target. When visibility is low, targets that are located at distances that exceed the visibility cannot be detected in the bit map. Therefore, the target that is nearest to the camera is located first. The pixel data in the region where the target is expected to be located is processed first in accordance with the cross-correlation techniques since that expected position in the bit map has the highest probability of locating the target. However, winds can shift the camera 12 which will cause the targets to be located in different positions on the bit map. Hence, the cross-correlation techniques may be used in other locations on the bit map if the initial target is not located. Additionally, first target 18 has a different signature than the other targets so that the cross-correlation techniques can uniquely identify the target 18 from the other targets.

At step 88 of FIG. 11, the other targets are located by referencing the known positions of the other targets to the location of the first target and by cross-correlation techniques that are designed to ensure that each of the targets has been properly located. At step 90, the bit map is segmented so that only the pixels that represent the images of the targets are saved and the remaining portion of the bit map is discarded.

At step 92, an edge operator is applied to the segmented portions of the bit map to generate contrast signals E(j,k). The edge operator is described as follows:

$$E(j,k)=|X|+|Y| \qquad \text{eg. (2)}$$

where $$X=(p_2+2p_3+p_4)-(p_0+2p_7+p_6)$$

$$Y=(p_0+2p_1+p_2)-(p_6+2p_5+p_4)$$

and where the pixels surrounding the neighborhood of the pixel F(j,k) are numbered as follows:

| $p_0$ | $p_1$ | $p_2$ |
|---|---|---|
| $p_7$ | $F(j,k)$ | $p_3$ |
| $p_6$ | $p_5$ | $p_4$ |

E(j,k) is the edge value obtained for the pixel location of F(j,k). The original Sobel operator is expressed as $$G(j,k) = \sqrt{X^2 + Y^2}$$

and requires more computation time than the above described operator due to the square root and square computations.

At step 94, the computer 16 generates a representative contrast number $H_n$. $H_n$ is the average of a predetermined percentage of the highest contrast signals E(j,k) that are generated by the edge operator at step 92. In the representative contrast number $H_n$, the n is representative of the target number. For example, target 18 is target 1, target 20 is target 2, target 22 is target 3, target 24 is target 4, and target 26 is target 5. Hence, $H_1$ is the representative contrast number for target 18, while $H_2$ is the representative contrast number for target 20, etc. The representative contrast number can then be represented as follows:

$$H_n = \text{TopAvg}(E_n(j,k), c) \qquad \text{eg. (3)}$$

In the specific implementation of the present invention where there are five targets, i.e., n=1, 2, ... 5, and the top 3 percent of the highest contrast signals are to be averaged for each of the targets, the following applies:

$$H_n = \text{TopAvg}(E_n(j,k), 3) \text{ for } n=1, 2 \ldots 5 \qquad \text{eg. (4)}$$

$H_n$, in this case, essentially represents the average of the top 3 percent of the contrast values of each of the targets n. This averaging is performed to minimize the deviation by one or two pixels that are falsely recorded by the video camera 12 due to incorrectly calibrated charge couple devices or other sudden flashing effects in the image that are not caused by atmospheric visibility conditions. This averaging scheme operates as a robust protection mechanism for obtaining the highest contrast level signals from each target.

At step 96 of FIG. 11, the values of $H_n$ are plotted in a graph of contrast levels versus the distance x of each of the targets from the camera. In other words, a single value of $H_n$ is generated for each target and that contrast level value ($H_n$) is plotted against the distance x of that particular target from the camera. An example of an actual plot of data obtained is shown in FIG. 12. $H_n$, which is indicated as the maximum edge representation, is plotted against x, which is the distance of the target from the camera, which is shown as the computational visual range. As can be seen, data points are indicated for each of the targets which are located at 40 meters, 50 meters, 100 meters, 150 meters, 200 meters, and 300 meters. As can be seen from the plot of these data points, an exponential curve is generated as shown in FIG. 12.

Figure 12:
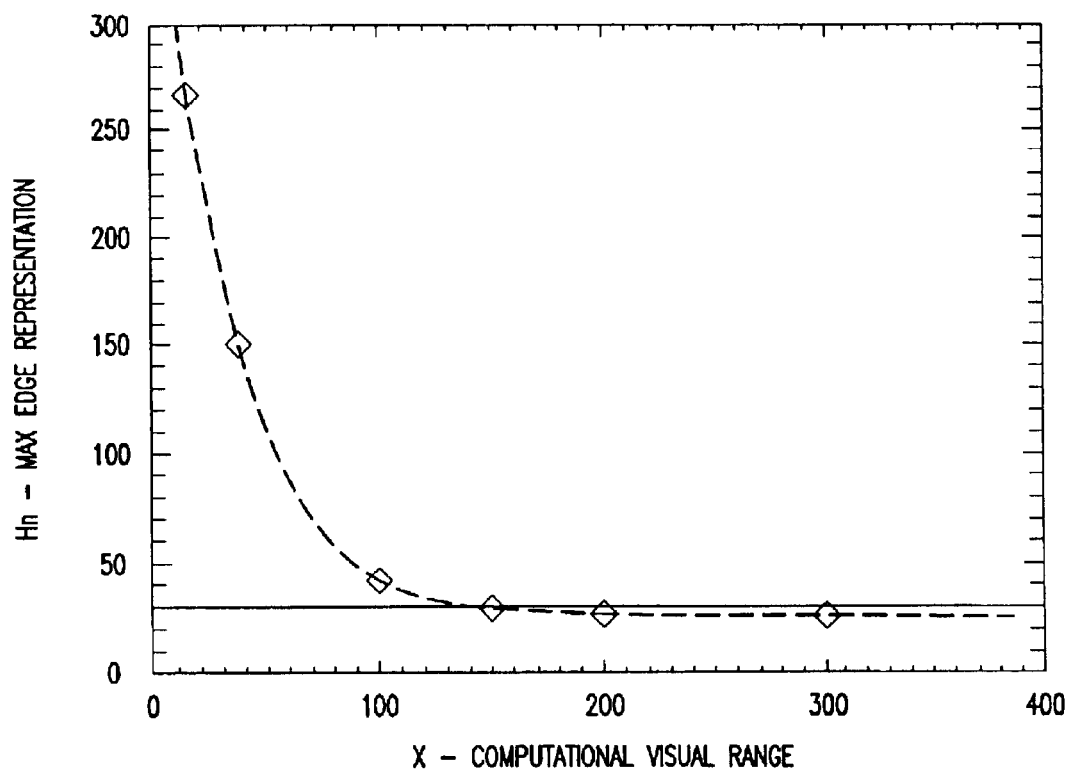
FIG. 12 is a graph of $H_n$ versus x.

At step 98 of FIG. 11, the computer 16 uses curve fitting techniques with the data points $H_n$ to generate the exponential curve illustrated in FIG. 12. In this manner, the constants $a_0$, $a_1$ and $a_2$ are determined for the exponential equation:

$$f(d) = a_0 e^{-a_1 d} + a_2 \qquad \text{eg. (5)}$$

where d is the distance of the target from the camera. The exponential curve illustrated in FIG. 12, is representative of the value of $H_n$ at any given distance d. A least squares fitting technique can be used to generate the exponential curve, such as disclosed by J. M. Ortega and W. G. Rheinboldt, *Iterative Solution of Non-Linear Equations and Several Variables*, Academic Press, Inc., San Diego, Calif., 1970. The curve f(d) illustrated in FIG. 12 represents the highest contrast levels, on average, versus the known distances of the targets from the camera.

Step 100 of FIG. 11 determines the atmospheric visibility. The atmospheric visibility is defined, in accordance with the present invention, as the distance where the edges of the contrasting portions of the target are degraded such that these edges are no longer distinguishable from the edges of the background noise. Referring to FIG. 12, the horizontal line that is drawn approximately represents the level of the contrasting edges that are no longer distinguishable from the background noise. This level of $H_n$ that is represented by the horizontal line is the threshold level of f(d), which is referred to as $f_{th}$. The visibility v can then be calculated as follows:

$$V = \frac{\ln[(f_{th} - a_2)/a_0]}{a_1} \qquad \text{eg. (6)}$$

As can be seen from FIG. 12, the threshold value of $H_n$ that is indicated by the horizontal line intersects the exponential curve at a distance x equal to 147 meters, which is the measured atmospheric visibility. This visibility can also be determined by detecting when the slope of the exponential curve reaches a predetermined minimum value, for example, a predetermined value of slope can be selected at which the exponential curve f(d), illustrated in FIG. 12, reaches a predetermined value. The value of x at that slope can then be determined which is the visibility measurement.

The advantages of generating atmospheric visibility measurements in accordance with the present invention are that the visibility measurements that are obtained in accordance with the present invention are based on recognition of visual features of targets, i.e., contrasting portions of the targets, and no special calibration is required for different types of atmospheric variations such as fog, rain, snow, smog, as is the case for scattered light measurements. Additionally, since the present invention uses an average of the highest contrast levels for each target, the results are not dependent on the target size, or the design, or shapes of the target, as long as valid contrast level signals can be obtained from each target. Hence, damages to the target or partial changes in the target do not significantly affect the outcome of the visibility measurements. Further, measurements made in accordance with the present invention are not sensitive to variations resulting from the use of different types of cameras, zoom factors, camera resolution or other camera properties. Thus, camera replacement does not require recalibration of the computational method. Also, since the present invention generates a visibility measurement based on visual features, visibility measurements made in accordance with the present invention directly measure the visibility in accordance with the definition of visibility set forth above.

Figure 13:
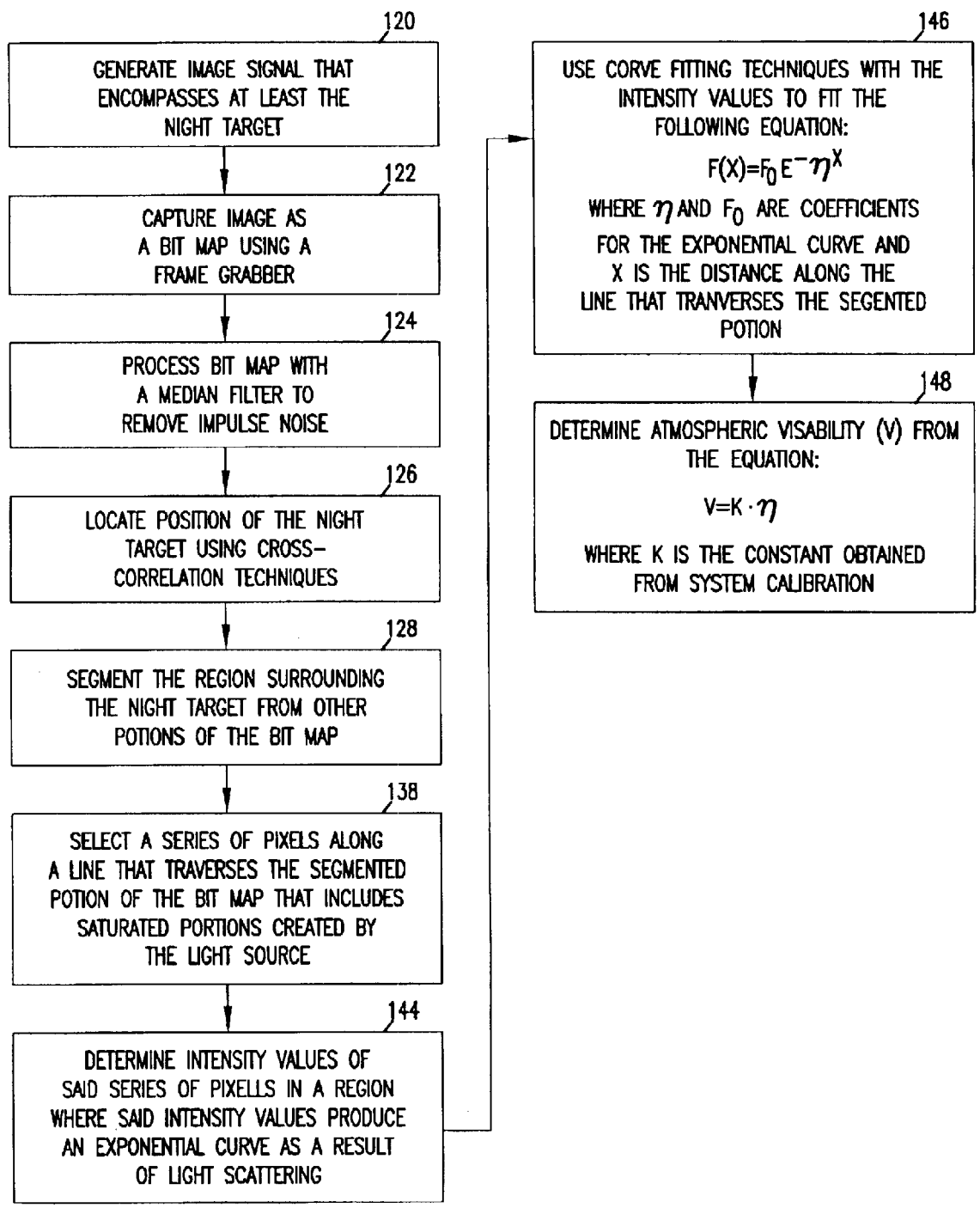
FIG. 13 is a flow diagram of the steps performed to measure atmospheric visibility in low light level conditions.

FIG. 13 is a flow diagram that illustrates the manner of detecting atmospheric visibility during low light level or nighttime conditions. Since most video cameras cannot see the targets or the contrasting portions of the targets at night, the present invention utilizes a light source mounted in a target to measure nighttime visibility. The night target illustrated in FIGS. 6 and 7 is utilized for the steps that are performed in FIG. 13 to detect nighttime visibility. At step 120 of FIG. 13, an image signal is generated by the video camera 12 that encompasses an area surrounding the night target. This image is then captured as a bit map using a frame grabber at step 122. At step 124, the computer 16 processes the bit map with a median filter, in the manner disclosed above, to remove impulse noise. The position of the night target is then located using a cross-correlation technique at step 126. At step 128, the region surrounding the night target is segmented from other portions of the bit map. A large enough region is segmented from the bit map to include the diffusion effect of the light source that is caused by the atmosphere.

Atmosphere visibility at night is closely related to the amount of scattered volume of the image from the saturated region of the light source. Saturated regions of the light source are identified as areas that are completely white and are physically located on the image in the central region of the light path of the light source.

Figure 14:
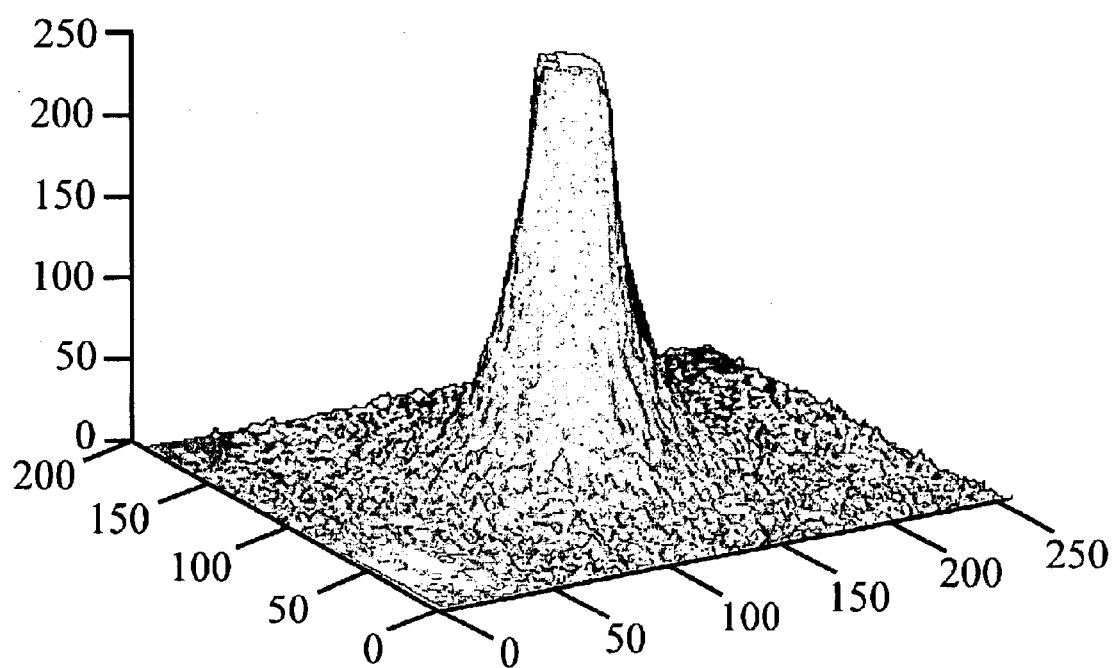
FIG. 14 is a three dimensional graph of light intensity values of the night target.

FIG. 14 is a three-dimensional plot of the detected light intensity of a bit map image in the segmented target region.

The three-dimensional plot illustrated in FIG. 14 shows the scattered volume in the X axis 132 and Y axis 134 of the light intensity levels that are plotted in the Z axis 136. As can be seen from FIG. 14, the saturated regions are shown at 130. The volume of the cone shape is directly related to the atmospheric visibility. As the volume increases, the visibility decreases. The characteristics of the cone shape illustrated in FIG. 14 are that the slope of the cone follows an exponential decay relation.

Figure 15:
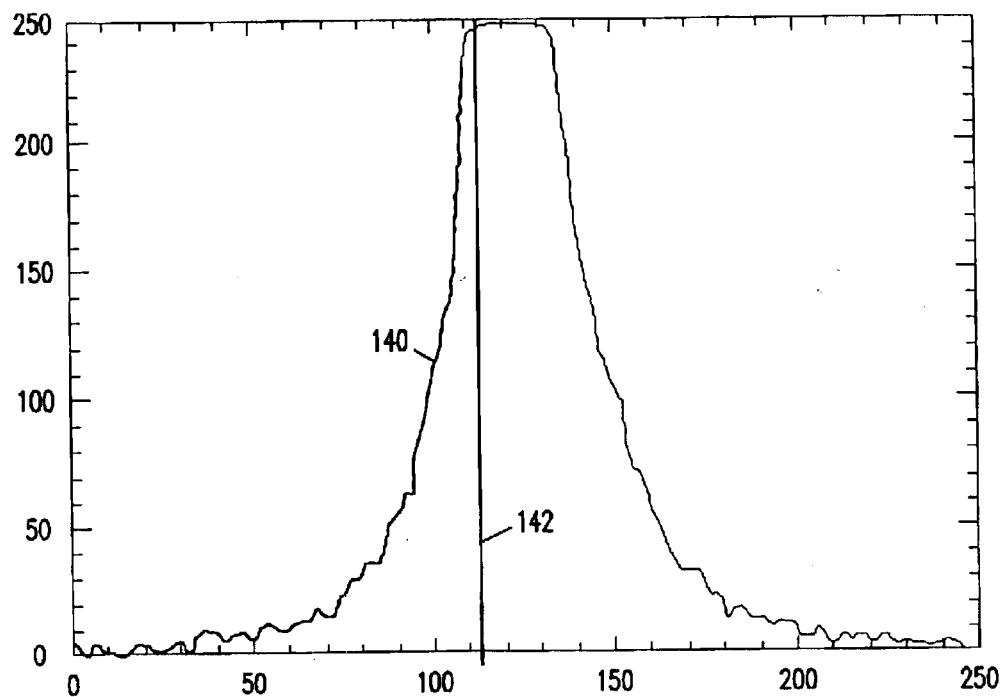
FIG. 15 is a two dimensional graph of light intensities that are taken from the three dimensional graph of FIG. 14.

FIG. 15 illustrates a plot of the intensity of the pixels that correspond to a cross-section along the X axis through the center of the cone 131 illustrated in FIG. 14. Referring to FIG. 13, at step 138 a series of pixels along a line that traverses a segmented portion of the bit map that includes the saturated portions is created by the light source. This corresponds to the plot of pixel intensities illustrated in FIG. 15. As shown in FIG. 15, an exponential curve 140 that represents the light intensity values of the scattered signal, is created by insertion of the ordinate line 142.

Referring to FIG. 13, at step 144, intensity values of the series of pixels corresponding to exponential curve 140 (FIG. 15) are determined in a region where the intensity values produce an exponential curve as a result of the light scattering. At step 146 of FIG. 13, curve fitting techniques are used with the intensity values illustrated in FIG. 15 of curve 140 to fit the following equation:

$$F(x)=F_o e^{-\eta x} \qquad \text{eg. (7)}$$

where $\eta$ and $F_o$ are coefficients for the exponential curve 140 and x is the pixel location from the left side of the plot illustrated in FIG. 15. As the area under the curve 140 becomes larger, the visibility becomes lower and the exponential curve becomes flatter. In general, it is determined from equation 7 that visibility is proportional to the coefficient $\eta$. In other words, the following relationship holds:

$$V \propto \eta \qquad \text{eg. (8)}$$

From equation 8, it can be deduced that the following is true:

$$V = k^* \eta \qquad \text{eg. (9)}$$

where k is a constant scaling factor that can be determined by calibrating the night vision device of the present system and V is the measured visibility at night. Referring to FIG. 13, the computer 16 determines the value for the constant k by using calibration factors. The constant k is dependent upon the intensity of the light source and properties of the video camera 12 such as resolution. Therefore, the coefficient $\eta$ must be known to compute the visibility in accordance with equation 9.

One way of determining the constant k is using a SLM. Since SLMs are relatively accurate under fog, the SLM can be used as a reference to estimate the constant k. In accordance with this process, the visibility is first measured using a SLM under foggy conditions which would give the value V. Then, using the processes disclosed above, the value of constant $\eta$ can be determined. Since the values of V and $\eta$ are known, k can be computed using equation 9.

However, since SLMs are generally expensive and the visibility cannot be measured until the value of the constant k is found on a foggy night, other solutions may be more advantageous. For example, a standard calibration mask, such as illustrated in FIGS. 9–10, can be used to generate a known amount of light scattering. A mask such as mask 74 of FIG. 9 can be designed to provide a predetermined visibility such as a visibility of 140 meters. To calibrate the night vision system of the present invention, the mask is placed in the light path of the day/night target 18 as illustrated in FIGS. 9 and 10. In total darkness on a clear night, an image of the light source can be captured and the process described above can be carried out to obtain a value for the constant $\eta$. In this case, since both $\eta$ and V (140 meters) are known, k can be calculated from equation 9 to calibrate the system.

A close review of equation 7 raises some interesting questions. Equation 7 can be rewritten as follows:

$$F(x)/F_o = e^{-\eta x} \qquad \text{eg. (10)}$$

This looks very similar to the equation that describes the contrast ration of a black object in accordance with the exponential decay law described by S. Q. Dauntley, "The Reduction of Apparent Contrast by the Atmosphere," *J. Opt. Soc. Am.*, vol. 38, 179–191. As disclosed by Dauntley, infra:

$$C/C_o = e^{-\sigma d} \qquad \text{eg. (11)}$$

Where $C_o$ is the inherent contrast against the sky, that is, the contrast measured at the target, C is the apparent contrast of the target observed at a distance d, and $\sigma$ is the atmospheric attenuation coefficient (extinction coefficient). A comparison of equations 10 and 11 allows one to deduce that contrast exists at night and that the light source of target 18 allows the system of the present invention to measure contrast. The existence of contrast at night and the ability to measure that contrast has not been known in the prior art.

Figure 16:
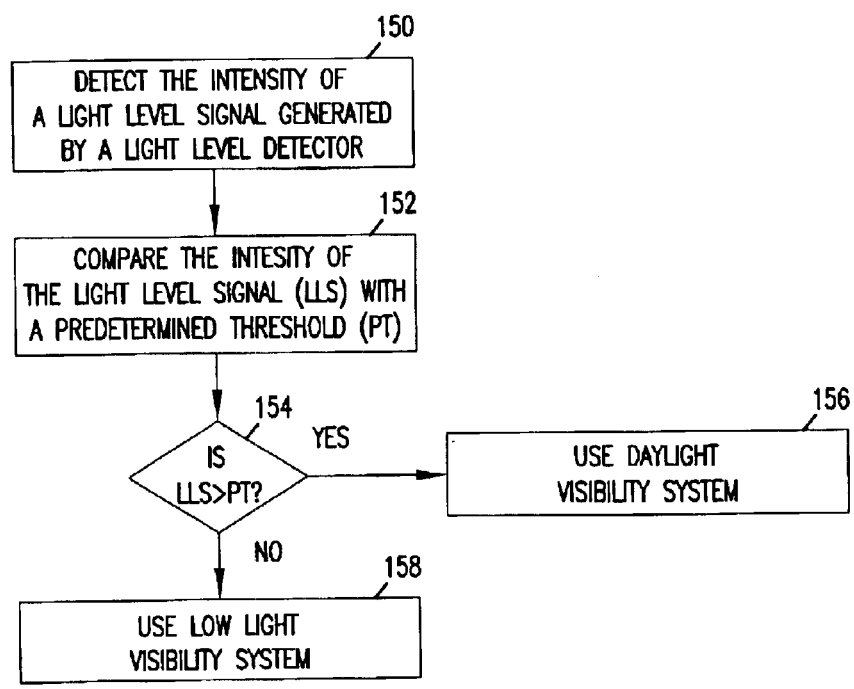
FIG. 16 is a flow diagram illustrating one method of selecting an atmospheric visibility measurement system.

Since the present invention uses two different methods for determining visibility, i.e., one method for determining daytime visibility and another method for determining visibility at night, an automated way of determining which method to use is advantageous. One method can employ a light sensor to determine the amount of light and thereby switch the system for determining whether to use the visibility measurement system for daylight hours or the visibility measurement system for night. FIG. 16 is a flow chart that discloses the steps of this method. At step 150 the intensity of a light level signal generated by a light detector such as light level detector 11 of FIG. 1 is detected by the system. The intensity of the light level signal is then compared with the predetermined threshold at step 152. At step 154 a decision is made as to whether the light level signal is greater than the predetermined threshold. If it is, the daylight visibility system is used as step 156. If it is not, the low light visibility system is utilized as step 158 to measure atmospheric visibility. However, this approach requires an additional light sensor and it adds additional cost and complexity to the system.

Figure 17:
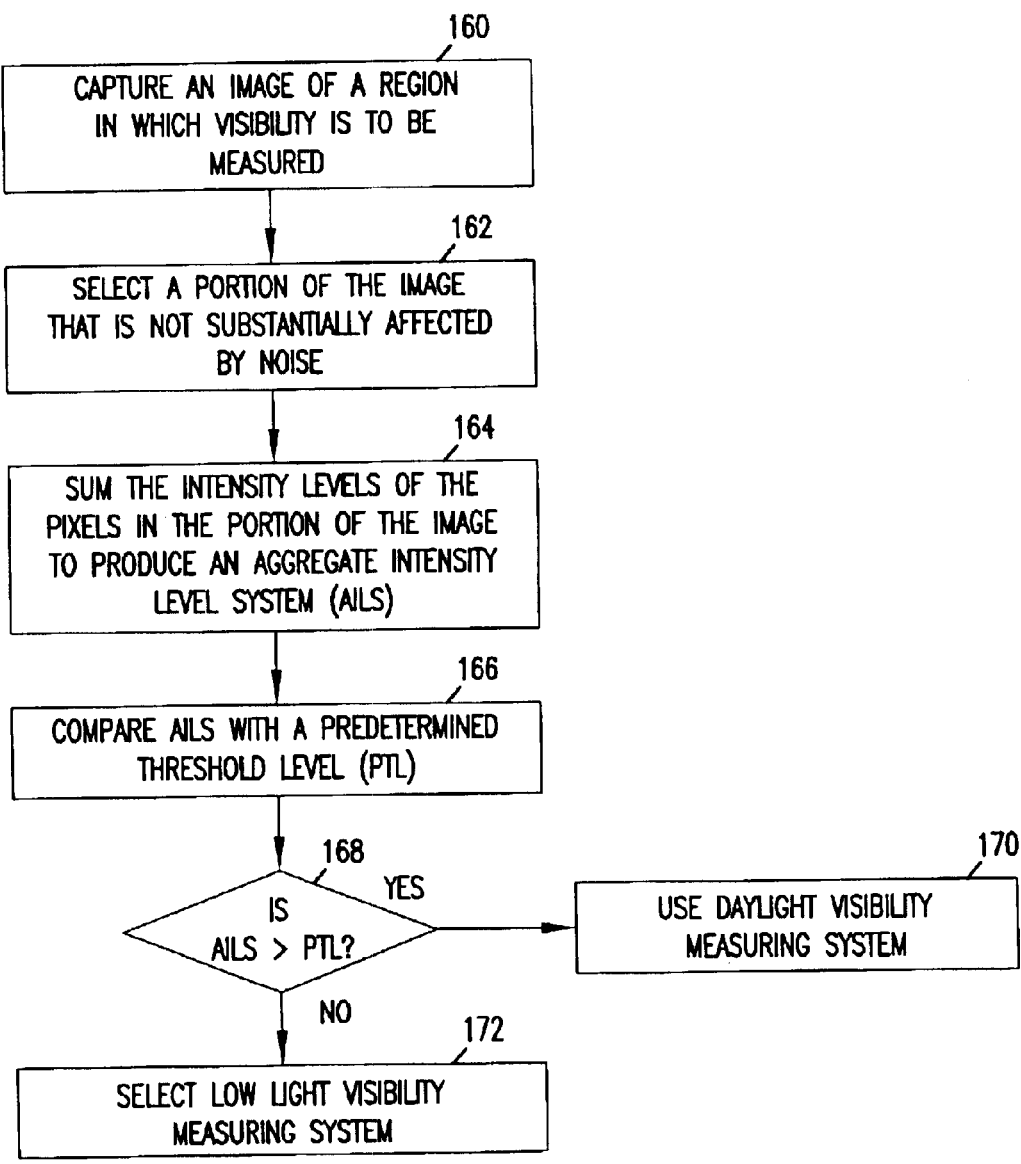
FIG. 17 is a flow diagram illustrating another method of selecting an atmospheric visibility measurement system.

Another method of automatically selecting the detection system is to generate a sum signal of the light intensity of a portion of the captured image, such as an area where trees or vegetation is present and other interfering factors are not present, such as car headlights, etc. A threshold value can then be generated based on the light intensity signal and the day or night method can be selected accordingly. FIG. 17 is a flow diagram illustrating the steps of selecting a visibility system in accordance with this method. At step 160, an image of a region which visibility is to be measured is captured by the camera 12. A portion of the image that is not substantially affected by noise is then segmented from the rest of the image at step 162. At step 164, the intensity levels of the pixels in the segmented portion of the image are added together to produce an aggregate intensity level signal. At step 166, the aggregate intensity level signal is compared with a predetermined threshold level. At step 168, a decision is made as to whether the aggregate intensity level signal is greater than the predetermined threshold level. If it is, the daylight visibility measurement system is selected at step 170. If it is not, the low light visibility measurement system is selected at step 172.

Figure 18:
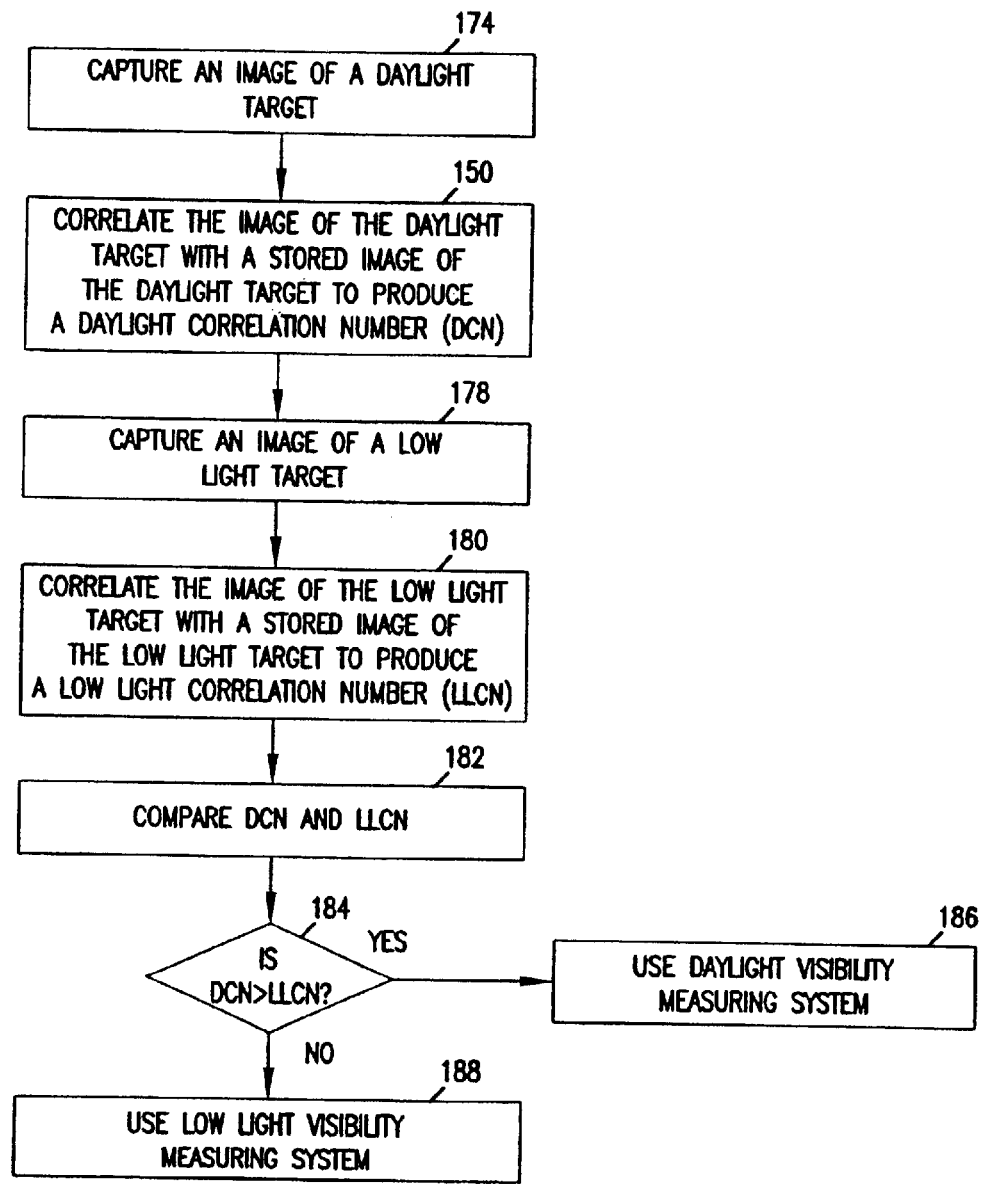
FIG. 18 is a flow diagram illustrating still another method of selecting an atmospheric visibility measurement system.

A third alternative method using correlation can be employed. According to this method, the targets are initially located in the manner described above. Then, a correlation process is performed for the day targets using a stored pattern. A similar correlation is then performed for the night target. A decision is then based on the more strongly correlated result. FIG. 18 is a flow diagram illustrating the steps for carrying out this method of selecting an atmospheric visibility measurement system. At step 174, an image of a daylight target is captured by the camera 12 and the frame grabber. At step 176, this image of the daylight target is then correlated with a stored image of the daylight target to produce a daylight correlation number. At step 178, an image is captured of the low light target. At step 180, the image of the low light target is correlated with the stored image of the low light target to produce a low light correlation number. At step 182, the daylight correlation number is compared to the low level correlation number. At step 184, the decision is made as to whether the daylight correlation number is greater than the low light correlation number. If it is, a daylight visibility measurement system is used at step 186. If it is not, a low light visibility measurement system is used at step 188.

The present invention therefore provides unique methods of determining visibility during both daylight and nighttime hours. Since the video camera that is used in accordance with the present invention records a visual image of the region in which atmospheric visibility is to be measured, that image includes all of the atmospheric effects that may affect visibility. In this manner, the video image not only represents the light scattering effect, but also includes all of the atmospheric conditions that may influence visibility. Additionally, video cameras display a field of view along the line of sight instead of a small region adjacent a SLM. Thus, the images represent a much larger area than that which is detected by SLMs. Therefore, the visibility computed using the video image based approach of the present invention is much less prone to local variations and atmospheric conditions. Further, the visibility measurements made in accordance with the daytime targets are based on the contrast levels that are detected for the targets. The visibility translation errors due to significant scattered light properties for different types of atmospheric particles are much smaller for the present invention than that of SLMs. Hence, the present invention does not require special calibration for atmospheric visibility that is affected by snow or rain, as is the case for SLMs.

The present invention also provides video images of the actual scene as a byproduct of the approach used by the present invention. Hence, these visual images can be used to verify the measured visibility by manual inspection. This verification capability using visual inspection is an important feature of the present invention in critical applications. Further, the camera lens system of the video camera has basically the same structure as the lens system of a human eye. Thus, if the camera is designed in the visual spectral range of the human eye, the video images recorded are a close representation of that which can be seen by the human eye. Since the visual features (contrasting portions of the targets) are used from the images to compute visibility, a more true definition of visibility can be measured rather than a single atmospheric condition (light scattering) that is measured by SLMs. Also, video cameras are already installed and used in many applications, such as traffic monitoring and transportation applications. These video cameras can be used to generate visibility measurements in accordance with the present invention to save additional cost. Lastly, a computation of visibility can be done from a remote location as long as the image signal or its digitized bit map data can be transmitted to the remote location where a computer is available.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention, except insofar as limited by the prior art.

I claim:

1. A system for measuring atmospheric visibility, comprising:
   a video detector that is aligned to detect an image having contrasting portions, the video detector configured to generate a signal indicative of contrast levels of said contrasting portions of the image; and
   a processor that generates a representative contrast number from said contrast levels, and that generates a nonlinear curve based on said representative contrast numbers and a distance value for each contrasting portion, and that generates a visibility number based on the intersection of the nonlinear curve with a lower threshold.

2. The system of claim 1 wherein said nonlinear curve is an exponential curve.

3. The system of claim 1 wherein said video detector comprises a video camera and a frame grabber.

4. The system of claim 1 wherein said processor generates said representative contrast number by determining an average of a predetermined percentage of the highest of said contrast levels detected by said video detector.

5. The system of claim 4 wherein said predetermined percentage is approximately three percent.

6. A system for measuring atmospheric visibility comprising:
   an image detector disposed at said predetermined location that is aligned to view a plurality of objects and that generates an image signal that is indicative of contrast levels of said objects; and
   a processor that generates a visibility range measurement by determining a distance at which said contrast levels can just be distinguished based on the slope of an exponential curve that is representative of contrast levels for each of said objects versus said distance of said objects from said detector.

7. The system of claim 6 wherein said plurality of objects comprise a plurality of targets having visible contrasting portions, said plurality of targets disposed such that each target of said plurality of targets is disposed in a predetermined region at a distance from a predetermined location.

8. The system of claim 7 wherein said plurality of targets comprises more than two targets.

9. The system of claim 7 wherein said plurality of targets have a size that varies in accordance with said distance of said target from said predetermined location so that said plurality of targets have an image size at said predetermined location that is approximately equal.

10. The system of claim 7 wherein the color of said targets are composed of black and white.

11. A method of measuring atmospheric visibility in a region measured from a predetermined location comprising the steps of:

generating image signals of a plurality of objects, said objects disposed in said region at distances from said predetermined location and defining contrasting portions of the image, said image signal having intensity levels that are indicative of said contrasting portions;

generating contrast signals from said intensity levels of said image signals that are representative of contrast levels that are detected for said plurality of objects;

generating an average high contrast signal that as representative of an average of a predetermined percentage of highest contrast levels of said contrast signal for said plurality of objects;

processing the average high contrast signal to generate an atmospheric visibility measurement.

12. The method of claim 11 wherein said step of processing the average high contrast signal comprises:

generating an exponential curve that is representative of said average high contrast signal for said plurality of objects versus distance of said plurality of objects from said predetermined location;

determining a location on said exponential curve at which said contrast levels can just be detected; and generating an atmospheric visibility measurement from said location on said exponential curve.

* * * * *